United States Patent
Spitaels et al.

(10) Patent No.: US 8,184,840 B2
(45) Date of Patent: May 22, 2012

(54) COMBINED SET COMPRISING A VIBRATOR ACTUATOR AND AN IMPLANTABLE DEVICE

(75) Inventors: Hartmut Spitaels, Niel (BE); Andrzej Zarowski, Niel (BE); Nick Van Ruiten, Niel (BE)

(73) Assignee: 3Win N.V., Niel (BE)

( * ) Notice: Subject to any disclaimer, the term of this patent is extended or adjusted under 35 U.S.C. 154(b) by 840 days.

(21) Appl. No.: 12/064,812

(22) PCT Filed: Aug. 22, 2006

(86) PCT No.: PCT/EP2006/065569
§ 371 (c)(1),
(2), (4) Date: Oct. 7, 2008

(87) PCT Pub. No.: WO2007/023164
PCT Pub. Date: Mar. 1, 2007

(65) Prior Publication Data
US 2009/0141919 A1    Jun. 4, 2009

(30) Foreign Application Priority Data
Aug. 22, 2005 (EP) .................................. 05107702

(51) Int. Cl.
H04R 25/00 (2006.01)
A61F 2/18 (2006.01)
A61K 9/22 (2006.01)
(52) U.S. Cl. .......... 381/326; 600/25; 623/10; 604/891.1
(58) Field of Classification Search ............... 600/25; 623/10; 604/891.1; 381/326
See application file for complete search history.

(56) References Cited

U.S. PATENT DOCUMENTS

| | | | | |
|---|---|---|---|---|
| 3,870,832 A | * | 3/1975 | Fredrickson | 600/25 |
| 5,085,628 A | * | 2/1992 | Engebretson et al. | 600/25 |
| 5,498,226 A | * | 3/1996 | Lenkauskas | 600/25 |
| 5,531,787 A | * | 7/1996 | Lesinski et al. | 623/10 |
| 5,772,575 A | * | 6/1998 | Lesinski et al. | 600/25 |
| 5,984,859 A | * | 11/1999 | Lesinski | 600/25 |
| 7,618,450 B2 | * | 11/2009 | Zarowski et al. | 623/10 |
| 7,730,892 B2 | * | 6/2010 | Merfeld et al. | 128/897 |
| 7,758,568 B2 | * | 7/2010 | Olsen | 604/891.1 |

FOREIGN PATENT DOCUMENTS
EP   1 435 757   7/2004
WO   WO 94/17645   8/1994

OTHER PUBLICATIONS
International Search Report dated Jan. 12, 2007.

* cited by examiner

*Primary Examiner* — Elvin G Enad
*Assistant Examiner* — Andrew R Millikin
(74) *Attorney, Agent, or Firm* — Knobbe, Martens, Olson & Bear, LLP

(57) ABSTRACT

A combined set including a vibration actuator and an implantable device provided to be implanted in an inner ear part is disclosed. The implantable device has a surface in contact with an inner ear fluid when inserted in said inner ear part. The implantable device includes a frame having an inner wall and a slidably movable member having an outer wall which is connected to the vibration actuator. The slidably movable member is provided for transferring energy supplied by the vibration actuator from and towards the inner ear fluid by means of a translational movement. The slidably movable member is at least partially mounted inside the frame in such a manner that a gap extending between the inner wall of the frame and the outer wall of the member is less than or equal to 0.1 mm.

18 Claims, 13 Drawing Sheets

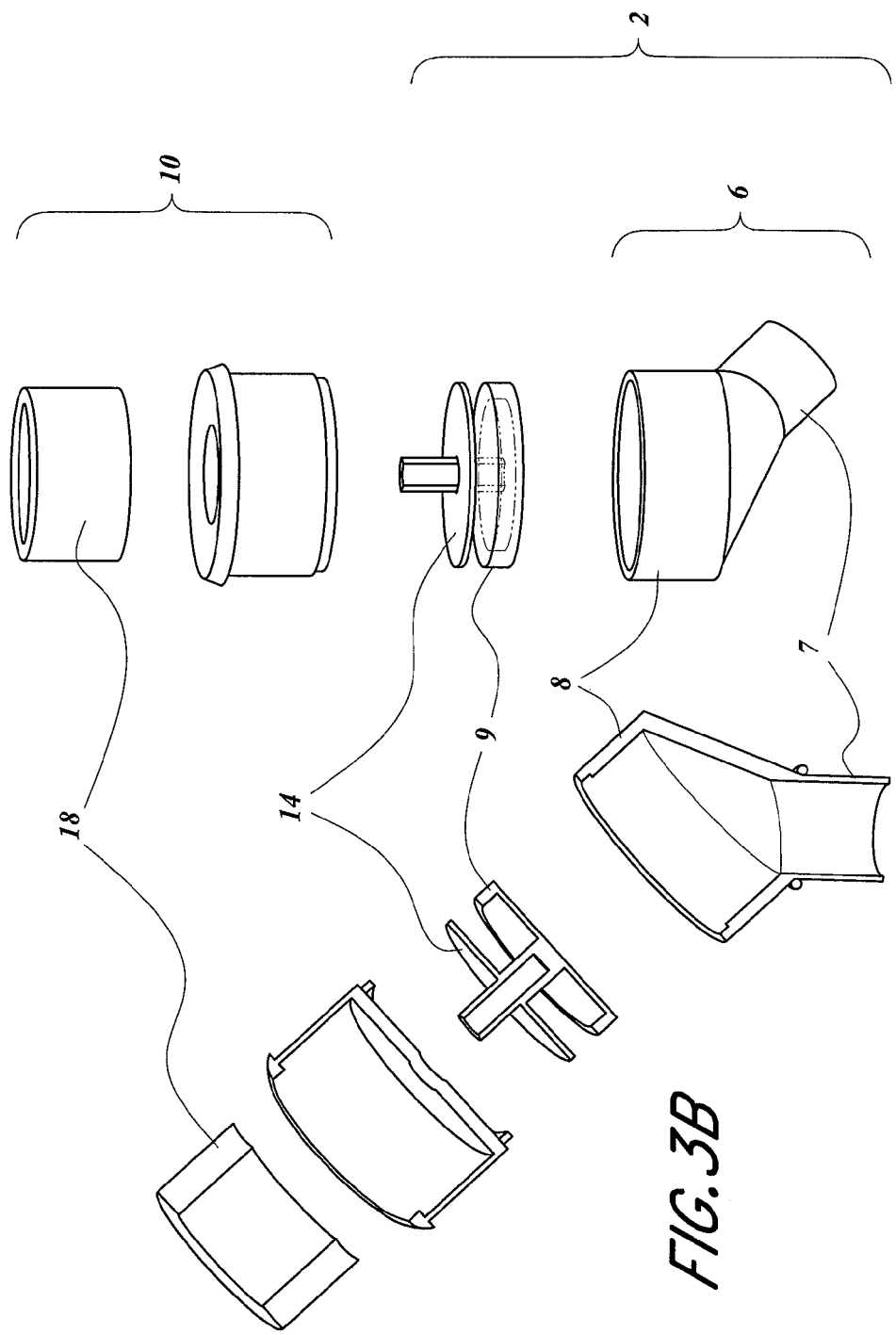

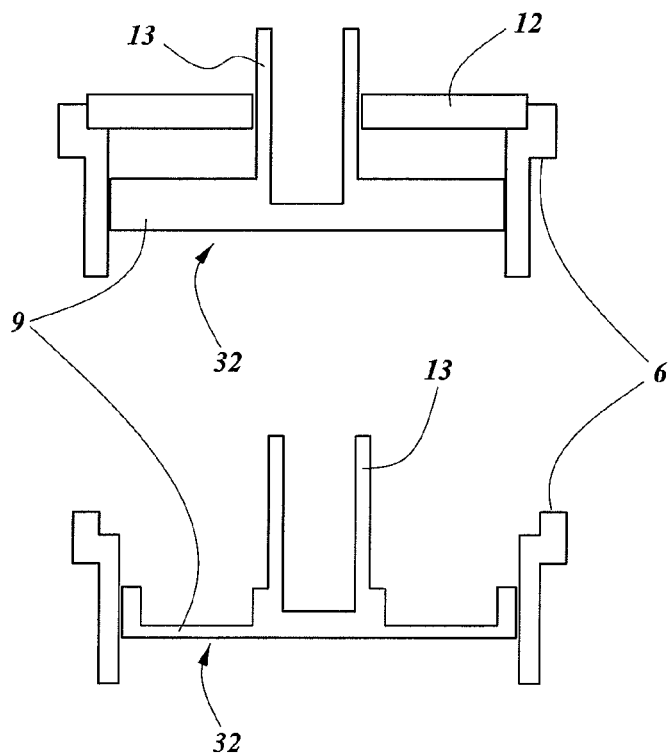
FIG. 4A
FIG. 4B
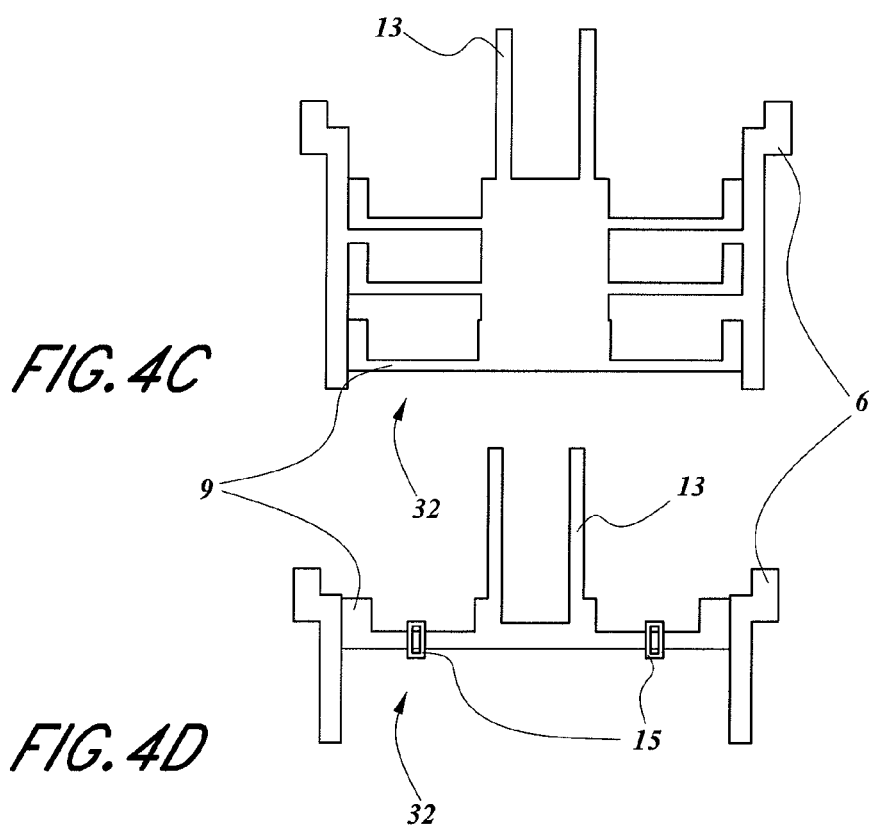
FIG. 4C
FIG. 4D

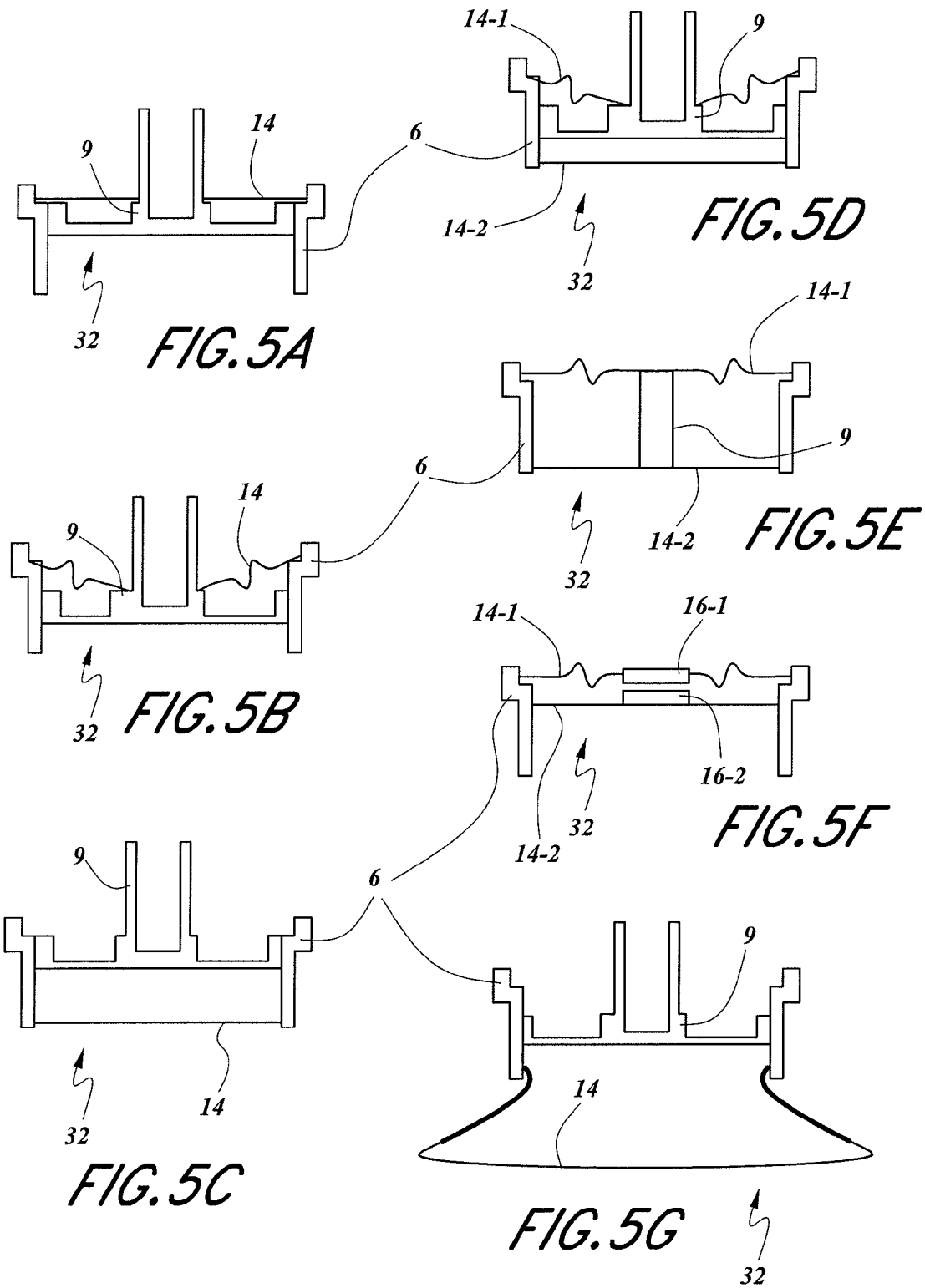

COMBINED SET COMPRISING A VIBRATOR ACTUATOR AND AN IMPLANTABLE DEVICE

CROSS-REFERENCE TO RELATED APPLICATIONS

This application is the U.S. National Phase under 35 U.S.C. §371 of International Application PCT/EP2006/065569, filed Aug. 22, 2006, which claims priority to EP 05107702.2, filed Aug. 22, 2005.

The present invention relates to a combined set comprising a vibration actuator and an implantable device provided to be implanted in an inner ear part formed by either a bony wall, an oval window, or a round window, said implantable device having a surface in contact with an inner ear fluid when inserted in said inner ear part, said implantable device comprising a frame having an inner wall and being provided to be at least partially inserted in said inner ear part, said implantable device comprising a slidably movable member having an outer wall and being connected to said vibration actuator, said slidably movable member being provided for transferring energy supplied by said vibration actuator from and towards said inner ear fluid by means of a translational movement.

Such a combined set is known from WO94/17645. In the known set the frame, made of a bio-compatible material, is provided for being inserted at least partially in an inner ear part. The frame is provided with a wall part formed by a flexible diaphragm, made of a bio-compatible material. The slidably movable member is formed by a piston, which is mounted on the flexible diaphragm. So the movement of the flexible diaphragm is communicated to the piston, which is in contact with the inner ear fluid. In such a manner, the movement of the piston causes an energy transfer, in particular mechanical and/or electrical and/or electromagnetic energy, towards said inner ear.

A drawback of the known set is that, when implanted, some inner ear fluid can leak along the outer wall of the piston. Indeed, the piston moves in an opening provided in an inner ear part formed by either a bony wall, an oval window, or a round window (e.g. the promontory). Applying such an opening is a surgical procedure, which is carried out manually in an area, which is difficult to access. The opening is therefore often slightly over-dimensioned, in order not to impede the translational movement of the piston. So some space is thus left open between the outer piston wall and the inner side of the opening in the promontory. When the slidably movable member moves out, in order to push the inner ear fluid out, some fluid flows through this space thereby causing a fluid leakage that bypasses the motion of the slidably movable member, which reduces the efficiency with which the slidably movable member vibrates the inner ear fluid. Moreover, as the piston moves inside the opening drilled in the bone, the movement of the piston could cause a wear of the bone. Finally a bone or tissue growth could narrow the opening thereby leading to an obstruction of the piston movement.

It is an object of the present invention to realise a combined set comprising a vibration actuator and an implantable device where substantially no inner ear fluid leakage could arise, where bone wear due to the movement of the slidably movable member is avoided and where, even when bone or tissue growth would occur, the latter would not affect the movement of the slidably movable member.

For this purpose, a combined set comprising a vibration actuator and an implantable device according to the invention is characterised in that said slidably movable member is at least partially mounted inside said frame in such a manner that a gap extending between said inner wall of said frame and said outer wall of said member is less than or equal to 0.1 mm. In contrast with the combined set known from WO94/17645, mounting the slidably movable member at least partially inside the frame allows defining a precise fit between the slidably movable member and the surrounding non-movable structure of the frame, thereby avoiding a fluid bypass that adversely affects the efficiency with which the slidably movable member vibrates the inner ear fluid. The frame and slidably movable member are machined and can therefore be accurately matched to each other, such that the gap between the inner wall of the frame and the matching outer wall of the slidably movable member is less than or equal to 0.1 mm. The slidably movable member can also be accurately aligned to the frame during assembly to further guarantee a precise fit. The fit between the slidably movable member and the surrounding non-movable structure, and therefore the performance of the implantable device in terms of the efficiency with which the inner ear fluid is vibrated, is thus guaranteed by design and by accurate manufacturing, and not by surgical skills. Tolerances better than 25 μm can be obtained with proper machining equipment, outperforming surgical tolerances by at least an order of magnitude. Moreover, as the slidably movable member is at least partially mounted inside said frame, the slidably movable member moves inside the frame and is therefore not affected by any bone or tissue growth, neither this movement could lead to a bone wear.

A first preferred embodiment of a combined set according to the invention is characterised in that said implantable device comprises at least one membrane applied within said frame and extending between said inner wall and said slidably movable member. The presence of the membrane further contributes to avoid leakages.

A second preferred embodiment of a combined set according to the invention is characterised in that said frame comprises a first segment and a second segment connected to each other. The two segments frame allows a more flexible implant.

A third preferred embodiment of a combined set according to the invention is characterised in that at least a part of a surface of said member and/or of said frame are coated with a coating suitable to improve tribological and/or wear resistance properties of said implantable device. This improves the bio-resistance of the set.

The invention will now be described in more details by referring to the drawings showing preferred embodiments of the combined set according to the invention. In the drawings:

FIGS. 3A to 3C illustrate an embodiment of the combined set, which allows an easy surgical implantation thereof;

FIG. 4A to 4D illustrate different variants of another embodiment of the implantable device where the member is formed by a piston;

FIGS. 5A to 5G show cross-sections of different embodiments of the implantable device in which at least one membrane is connected to the frame;

Figure 11A:
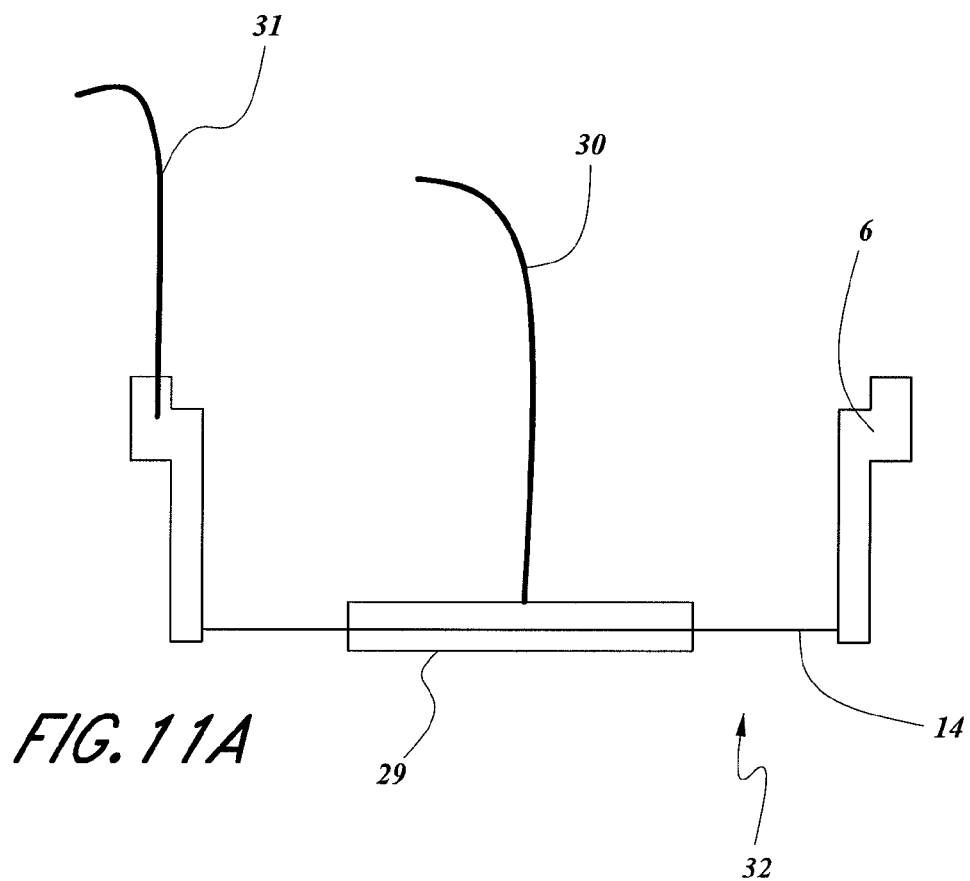
Figure 11B:
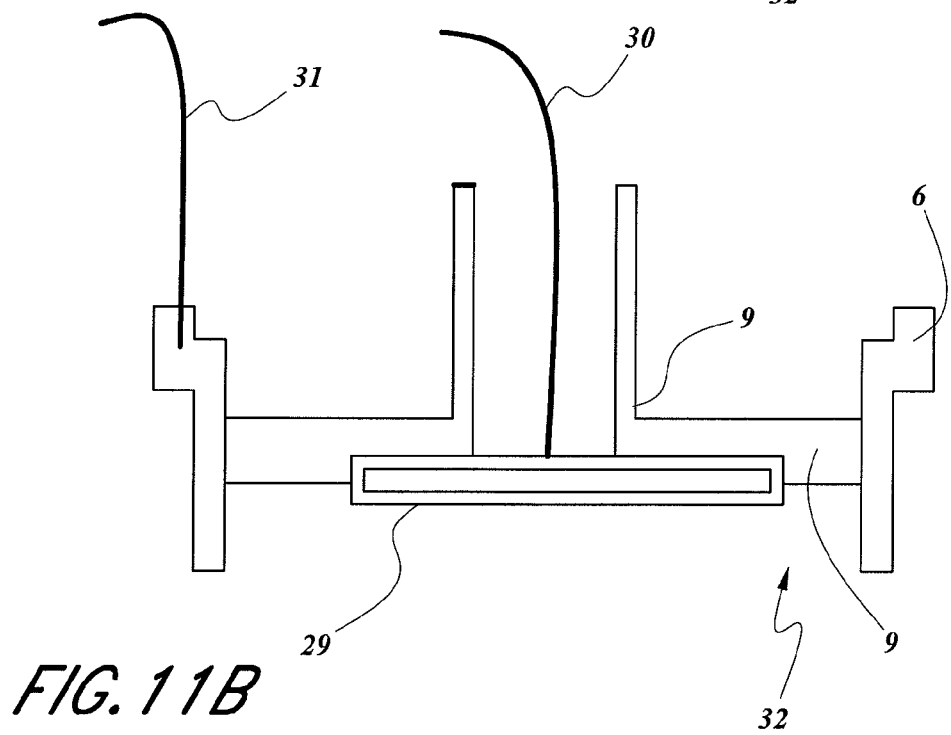
Figure 12B:
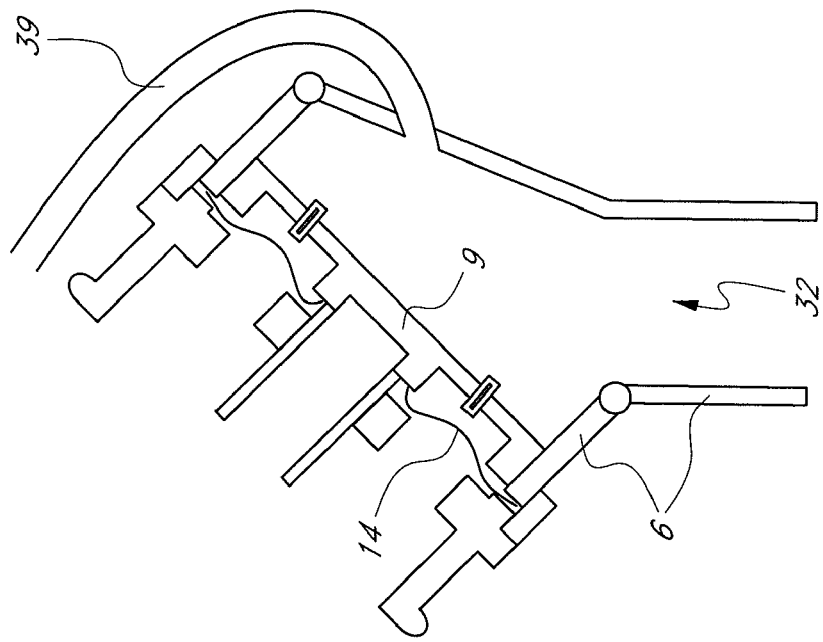
Figure 12A:
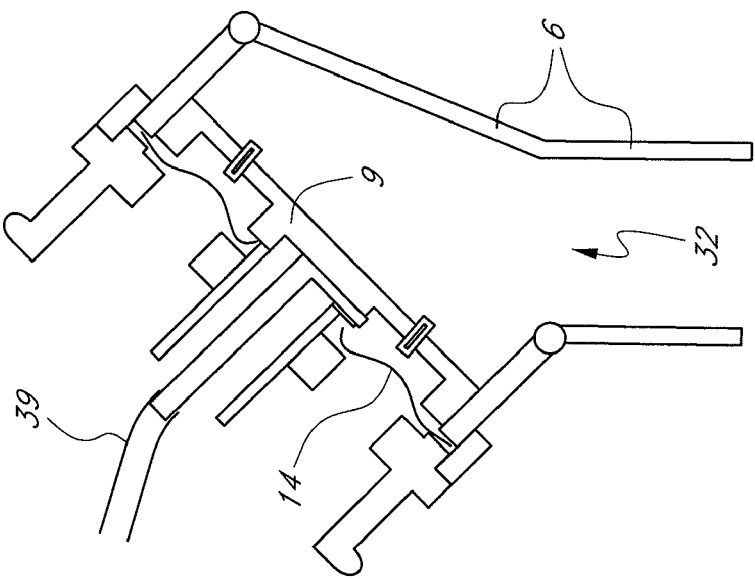

FIGS. 11A and 11B show a cross-section of a further embodiment of an implantable device as component of a combined set according to the invention, where the embodiment comprises an electrically conductive means provided to apply and/or sense electric signals directly to and from the inner ear fluids; and FIGS. 12A and 12B illustrate a further embodiment of the combined set provided with a tube element allowing a transfer of substances.

In the drawings a same reference has been allocated to a same or analogous element.

In the functioning of hearing aids a sufficient amount of energy has to reach the inner ear. In normal hearing, this amount of energy is related to the volume displaced by the footplate in the oval window. Due to acoustical pressure changes, the footplate vibrates and induces a travelling wave along the Basilar membrane. These travelling waves stimulate the sensory cells along the Basilar membrane. The higher the acoustical pressure at the footplate, the more volume the footplate displaces. The inner ear fluid being incompressible, this volume displacement has to be compensated at the round window. Thus the footplate and the round window produce nearly the same volume displacements, but in opposite phase. A hearing aid or hearing prosthesis can therefore be described in terms of its efficiency to generate volume displacement in the inner ear. In order to produce this volume displacement, energy is required. Using the hearing aid described in WO 2004/060015, which is hereby incorporated by reference, the energy is transferred to the inner ear fluid by means of a membrane. However the energy transfer obtained by using such a membrane is limited. The basis for this limitation is twofold:

(1) the membrane volume displacement is limited as it is bound by its elasticity;

(2) the very limited available space at the site of implantation.

The first statement is governed by the physics of membrane deformation. A membrane bulges out to displace a volume, which requires the membrane material to stretch laterally as the membrane is clamped at its outer edge. Membrane materials have a finite elasticity limit beyond which they deform plastically and then fail. A membrane also deforms mostly at its centre, and the deformation gradually decreases to zero at its sides, which contributes to a less optimal volume displacement for a given stroke. A piston-like volume displacement is optimal in this respect. This is not possible given the clamped boundary conditions. The present invention therefore proposes a solution by having a member, in particular formed by a piston, moving in a frame. This piston has the maximum volume displacement for a given stroke.

With respect to the second statement, the implantable device is optimally placed in the bony wall of the Scala Vestibuli of the inner ear. A less efficient energy transfer to the Basilar membrane is achieved when the implantable device is implanted in the Scala Tympani, due to energy loss towards the round window. The loss towards the oval window when implanted in the Scala Vestibuli, is less prominent because of the higher mechanical impedance of this oval window. This higher mechanical impedance is a result of the sum of the mechanical impedance of the oval window itself and the attached ossicies and tympanic membrane. The space available in the inner ear to make this artificial fenestrum to the Scala Vestibuli is limited both by anatomy and surgical access. The artificial fenestrum should be as small as possible to minimise the risk involved with surgery. These risks include destruction of inner ear structures, acoustical trauma and remnants of debris in the inner ear. In addition, the artificial fenestrum should preferably be round for minimal surgical complexity, to minimize the drilling time for implanting the artificial fenestrum and hence to minimise the time needed for the entire surgery. Furthermore, the area where the opening can be drilled is limited since it has to be accessed via the ear canal. As a result, the optimal area for implantation is the proximity of the oval window or the oval window itself.

The above constraints severely limit the design and dimensions of the implantable device. As a result, if a membrane were to be used, it cannot be dimensioned large enough to provide an adequate energy transfer.

Figure 1:
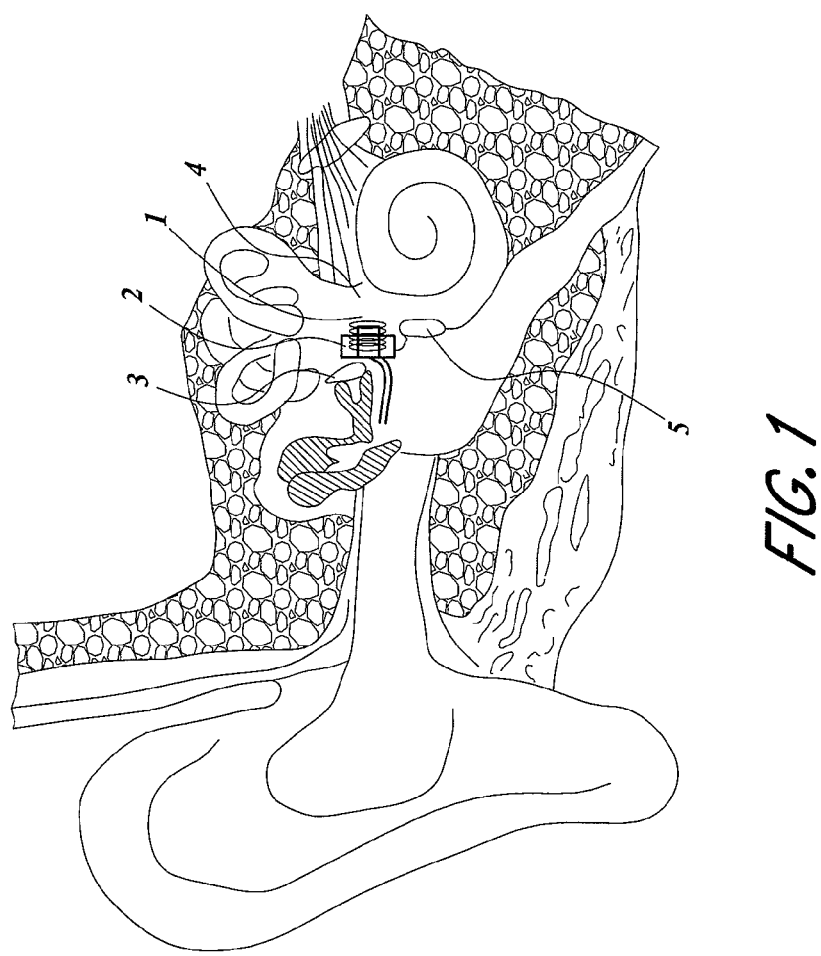
FIG. 1 shows the best location for implanting the combined set.

FIG. 1 shows the preferred location 1 for applying the combined set. This location 1 is next to the oval window 3 in the Scala Vestibulum. The combined set can also be implanted in other locations forming part of the inner ear, such as in other parts of the bony wall 4 of the inner ear, the bony wall of any of the semicircular canals, oval window 3 or the round window 5 or in a niche situated around them. The implantable device 2 is provided for acting on an exposed lining, for example the endosteal lining of the inner ear fluid spaces or directly on the inner ear fluid in order to transfer energy from and towards the inner ear.

Figure 2A:
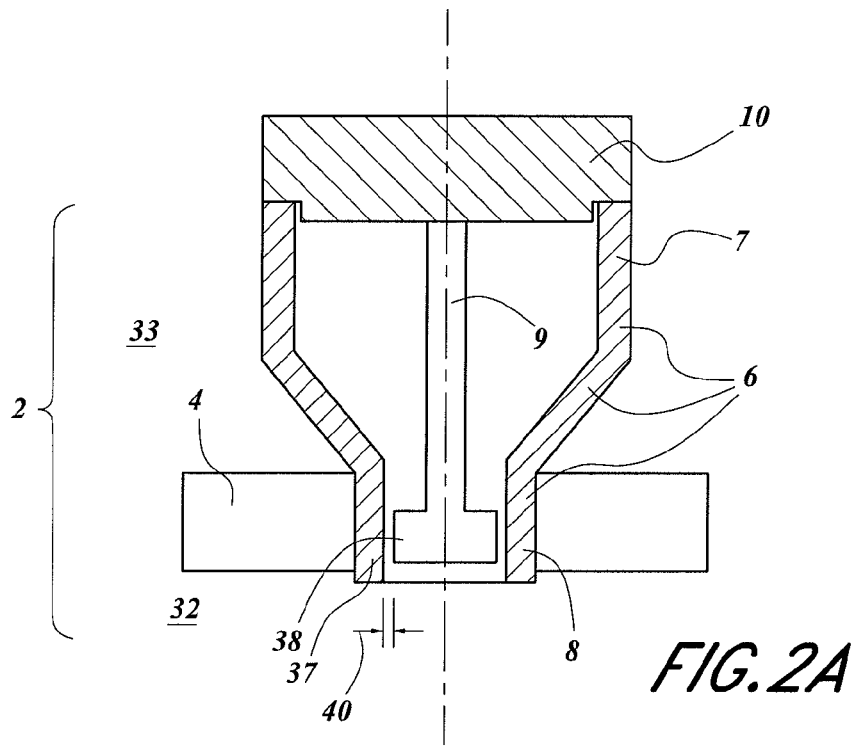
FIGS. 2A and 2B illustrate an embodiment of the combined set highlighting the narrow gap between the inner wall of the frame and the matching outer wall of the slidably movable member.
Figure 2B:
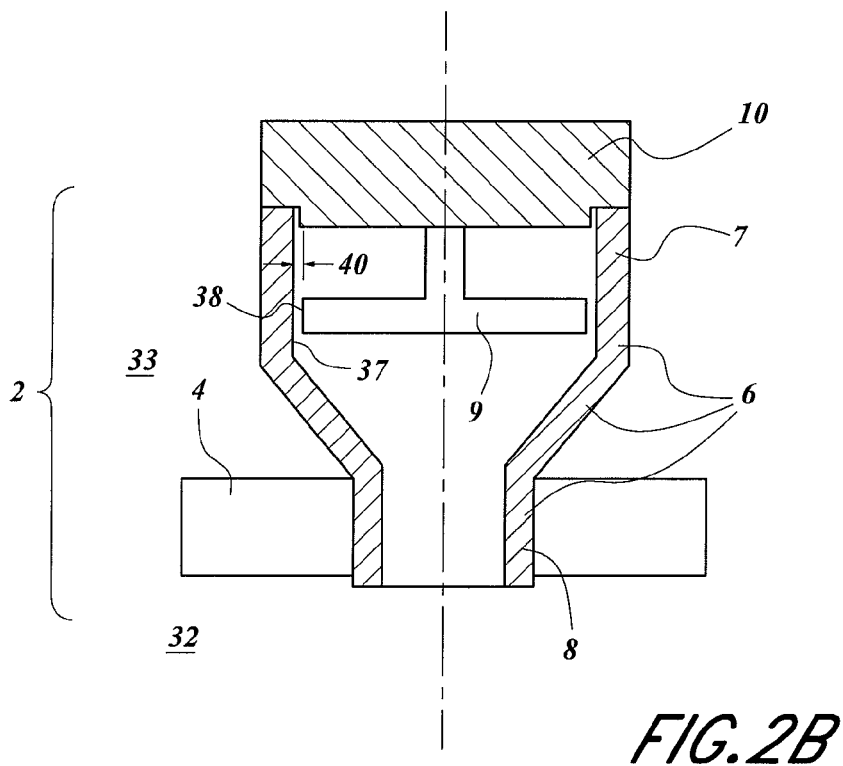

FIGS. 2A and 2B illustrate a cross section of two embodiments of the combined set according to the invention. The embodiment in FIG. 2B allows for an easy surgical implantation, while still addressing a large volume displacement. The middle ear 32 is separated from the inner ear side by a bony wall 4. The artificial fenestrum that needs to be applied in that bony wall 4 by the surgeon is minimised, by using a frame 6 comprising two segments connected to each other. According to a preferred embodiment, the first segment 7 has a smaller diameter than the second segment 8. There can also be a tapered transition between both segments.

The implantable device 2 of the present invention offers a solution to the problem of fluid bypassing the motion of the slidably movable member, which reduces the efficiency with which the slidably movable member vibrates the inner ear fluid 32. For this purpose the slidably movable member 9 is mounted inside the frame 6 in such a manner that a gap 40 extending between an inner wall 37 of said frame and an outer wall 38 of said slidably movable member 9 is less than or equal to 0.1 mm. Thus the gap 40 between the slidably movable member and the inner frame wall is rather small and only a negligible amount of fluid could leak through this gap. Moreover, as the slidably movable member is mounted inside the frame, there is no direct contact between the slidably movable member and the bone, thereby avoiding that the movement of the member would cause any bone wear or that a tissue or bone growth could come to hinder the movement of the member.

Figure 3A:
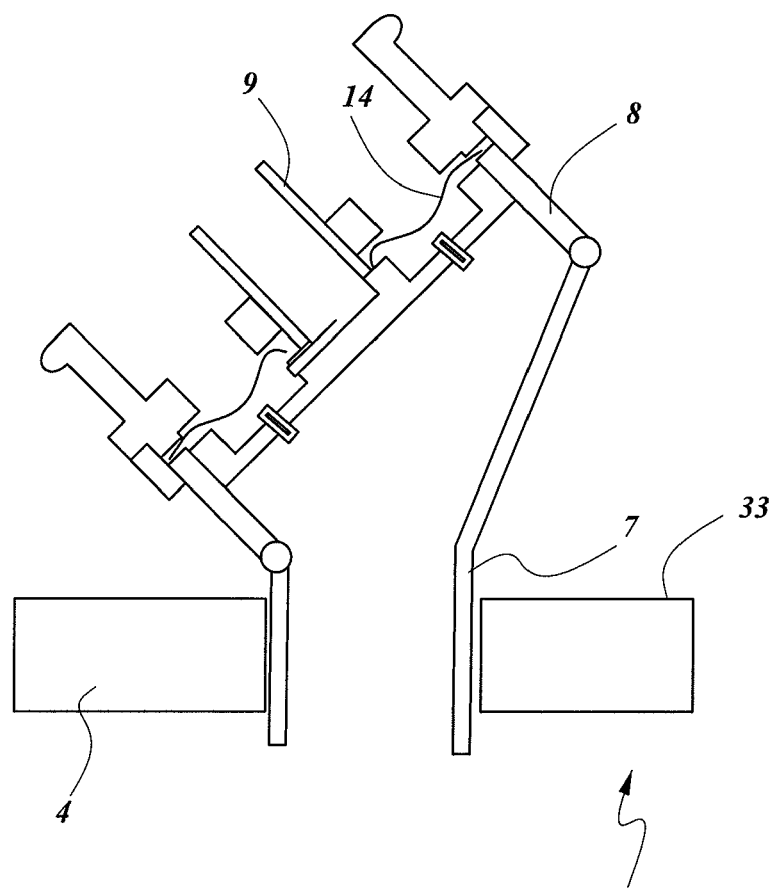

FIG. 3A is a cross sectional drawing and FIGS. 3B and C are 3-dimensional exploded views of another embodiment of the combined set according to the invention.

The first segment 7 with the smaller diameter is placed in the bony wall 4 of the inner ear. The diameter of this segment should be dimensioned to be optimal for the anatomical and surgical limitations as mentioned above. By having the first segment with the smaller diameter in the bony wall, the diameter of the opening to be drilled remains small, thereby reducing the probability to damage the inner ear.

The second segment 8 with the larger diameter contains the up- and downwards slidably movable member 9. The volume displacement imposed by this member will on its turn be transferred to the inner ear fluid 32 via the first segment 7 with the smaller diameter. Because this second segment is not implanted in the bony wall 4, the size is not limited by the constraints imposed by the earlier mentioned anatomical limitations of the inner ear and the surgical limitations. The diameter and size of this second segment is dimensioned on the one hand to create an optimal volume displacement and on the other hand to fit within the anatomy of the middle ear. This approach allows minimal invasive surgery.

In a variant of the two segments frame embodiment 6, the second segment 8 is inclined with respect to the first segment 7 so as to give the surgeon the possibility to optimally position the implantable device 2 relative to the middle ear structures. The orientation of the whole frame 6 in the inner ear part is obtained by rotating the latter around a central longitudinal axis of the first segment 7. This is particularly useful when the implantable device is used in a passive mode, i.e. when the energy is not artificially induced, but originates from the sound pressure present in the patient's ear canal and causing the eardrum and/or middle ear ossicles to vibrate. In this passive mode the vibration actuator is for example formed by the eardrum and/or middle ear ossicles and an interface 11 (see FIG. 9) provided for transferring the energy produced by the actuator to the member 9. The mentioned inclination allows an easier linking of this interface with the eardrum and/or middle ear ossicles.

In another variant of the embodiment with two segments, the inclination of the second segment 8 relative to the first segment 7 can be adapted. For this purpose the first and second frame segment are connected to each other by a hinge. This embodiment gives the surgeon additional freedom to optimally link the interface 11 between the member 9 and the eardrum and/or middle ear ossicles, when the implantable device is used in the passive mode.

The segments of the implantable combined set are preferably cylindrically or oval shaped to optimally accommodate the necessary volume in the middle ear. FIG. 3B shows an embodiment where an electromagnetic coil 18, which is part of a vibration actuator 10, is lodged inside the second segment of the frame. The actuator acts on the member 9 in order to transfer the generated vibration energy to the member, which on its turn will transfer it to the inner ear fluid. The member 9 is at least partially and slidably mounted inside the frame. The slidably movable member can accommodate a larger energy transfer than a membrane because the sliding member movement can be extended over a substantial part of the frame volume. This large piston stroke also allows compensating the large, inaudible but uncomfortable low-frequency pressure variations that occur e.g. during diving or flying.

A member 9 formed by a T-shaped piston is shown in the embodiment illustrated in FIG. 4A. The cross-section of the T-shaped piston is symmetric with respect to a central axis extending transversally through the piston. This symmetry allows minimisation of the mass and hence of the inertia. When actuating the piston at high frequencies in order to transfer energy to the inner ear fluids, the inertia of its mass becomes a significant proportion in the mechanical impedance. This mechanical impedance has to be minimised to allow an efficient energy transfer. At lower frequencies the impedance is predominantly resistive in this case. The inner ear fluids present in the space between the piston 9 and the frame 6 will cause a friction resistance to the movement of the piston. At higher frequencies inertial components have an increasing influence. Hence, as stated supra it is necessary to minimise the mass of every moving part in order to minimise the energy losses. For example by making the member substantially hollow.

FIG. 4A also shows a guidance 12 for the shaft 13 of the piston. This guidance is applied in the frame 6 and can also serve as a stop to limit the stroke of the piston. If the shaft has an asymmetric cross-section, this guidance has a hole with the same asymmetric cross-section and can prevent the piston from rotating around its axis. This limitation is particularly useful for protecting, while manipulating the implantable device 2, a membrane if connected to the member 9, as described hereinafter.

FIG. 4B shows a cross-section of the piston according to another embodiment with minimised inertia. According to this embodiment the piston comprises its shaft 13 and a thin head surface having an upstanding ridge.

FIG. 4C shows a cross-section of another embodiment in which the member 9 comprises a plurality of superposed pistons interconnected to each other and slidably mounted in the frame. Having more than one piston will further reduce unwanted leakage of the inner ear fluids. It is however known that the inner ear can compensate for a minor leakage by constantly producing inner ear fluids.

FIG. 4D shows a cross-section of another embodiment in which the piston comprises one or more holes 15 applied in its head surface. These holes can operate as mechanical filters resulting in a high-pass frequency characteristic of the implantable device 2. In such a manner, the low-frequency vibrations are attenuated, while the higher frequency content is transferred unaltered. The size of the holes 15 determines the friction between the piston and the inner ear fluid while acting on this fluid, and therefore the cut-off frequency of this high-pass characteristic. Instead of acting on the dimension of the holes it could also be possible to house inside the holes a vibration attenuating structure.

Part of the surface of this member 9 and/or the frame 6 may be coated with a coating suitable to improve the tribological and/or wear resistance properties of the implantable device. Said substance can be for instance polytetrafluoroethylene (PTFE=Teflon), diamond-like-carbon (DLC), cubic-boron-nitride (CBN). These coatings can be applied for instance with chemical vapour deposition or sputtering. The coating can also serve to minimise leakage of inner ear fluids. This coating could have for instance hydrophobic properties.

FIGS. 5A-G show cross-sections of different embodiments in which the leakage barrier means are formed by at least one membrane 14 which is connected to the frame 6 of the implantable device 2 in order to form a barrier between the middle ear and the inner ear fluids. The membrane extends between the inner wall of the frame and the movable member. The barrier created with this membrane prevents the leakage of inner ear fluids into the middle ear and prevents that the inner ear could be infected by an infection present in the middle ear. If the artificial fenestrum would not be made infection-impenetrable, an infection, for instance from a chronic ear disease, could result in cophosis. Therefore this embodiment is preferred for those pathologies where infection is likely. This membrane 14 is preferably made of titanium, an elastomer like silicone, or another bio-compatible material.

In a first variant of the embodiment provided with a membrane 14, as illustrated in FIG. 5A, the membrane 14 is connected to the member 9, in particular to the shaft of the piston. The flexibility of the membrane is designed as to follow the sliding movement of the member in the frame, and to have negligible mechanical impedance.

In the variant of the embodiment provided with a membrane 14 and illustrated in FIG. 5B, the membrane is corrugated and/or given a protuberant pre-shape, this in order to improve the flexibility of the membrane.

As shown in FIG. 5C, the membrane 14 is connected to the frame 6 and positioned downstream of the member 9 so as to contact the inner ear fluids when applied in the inner ear part. The latter embodiment could be combined with the one illustrated in FIG. 5A in order to obtain an implantable device with two membranes 14-1 and 14-2, as illustrated in FIG. 5D. A fluid could be present in the space delimited by both membranes 14-1 and 14-2.

In a variant of the embodiment with two membranes 14-1 and 14-2, as illustrated in FIG. 5E, both membranes are connected with the member 9 situated between the membranes.

Alternatively, as illustrated in FIG. 5F, each membrane 14-1 and 14-2 could be provided with a magnetic element 16-1 and 16-2 formed by permanent magnets and/or electromagnets. The magnetic elements are preferably coated and/or embedded within said membranes. Said magnetic elements being for instance a Ni—Fe alloy (Permalloy) or a Nd—Fe—B alloy. In this embodiment the magnetic elements form the member provided for transferring the energy to the inner ear fluid, so that it is not necessary that the magnetic elements are slidably mounted in the frame. The same applies to the embodiment where the member is applied inside the volume delimited by the two membranes.

Alternatively, as illustrated in FIG. 5G, the membrane 14 is expandable after introduction into an inner ear. The expanded membrane provides a larger functional surface facing the inner ear part where the implantable device is applied. This expanding allows for an increased volume displacement of the inner ear fluid.

Figure 6:
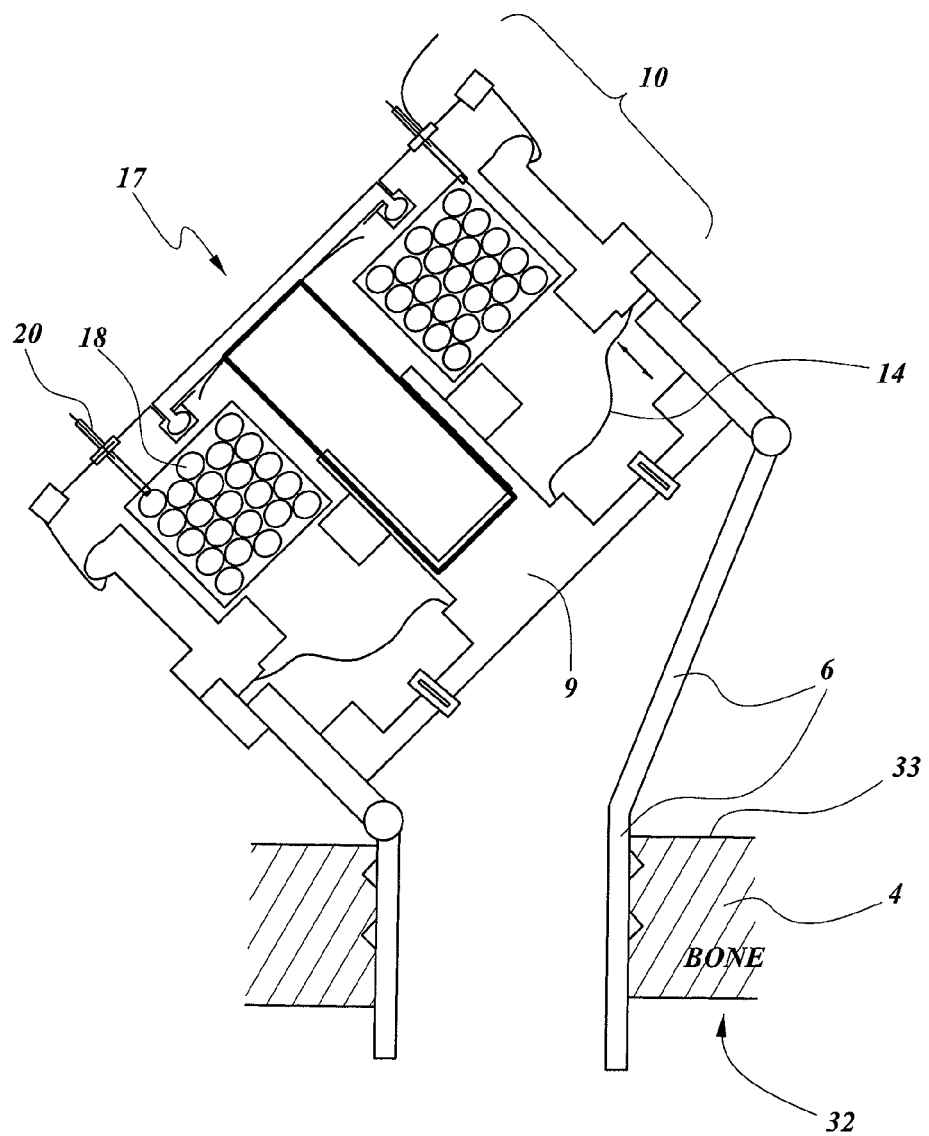
FIG. 6 illustrates an embodiment of the combined set according to the present invention and provided with an electromagnetic sensing and/or stimulating member.

FIGS. 6A and 6B illustrate in cross-section an example of the combined set according to the present invention and provided with an electromagnetic sensing and/or stimulating member 17. A coil 18 is placed inside the electromagnetic sensing and/or stimulating member and connected to insulated wires 20 carrying a stimulating electrical current. An alternating stimulating current through the coil creates a varying magnetic field which, for instance, in the presence of a static magnetic field, can cause a mechanical force that can vibrate the slidably movable member 9. The member 17 could also be used to sense the motions of the slidably movable member 9. Alternating movements of the member induce AC currents in the coil 18.

Figure 7:
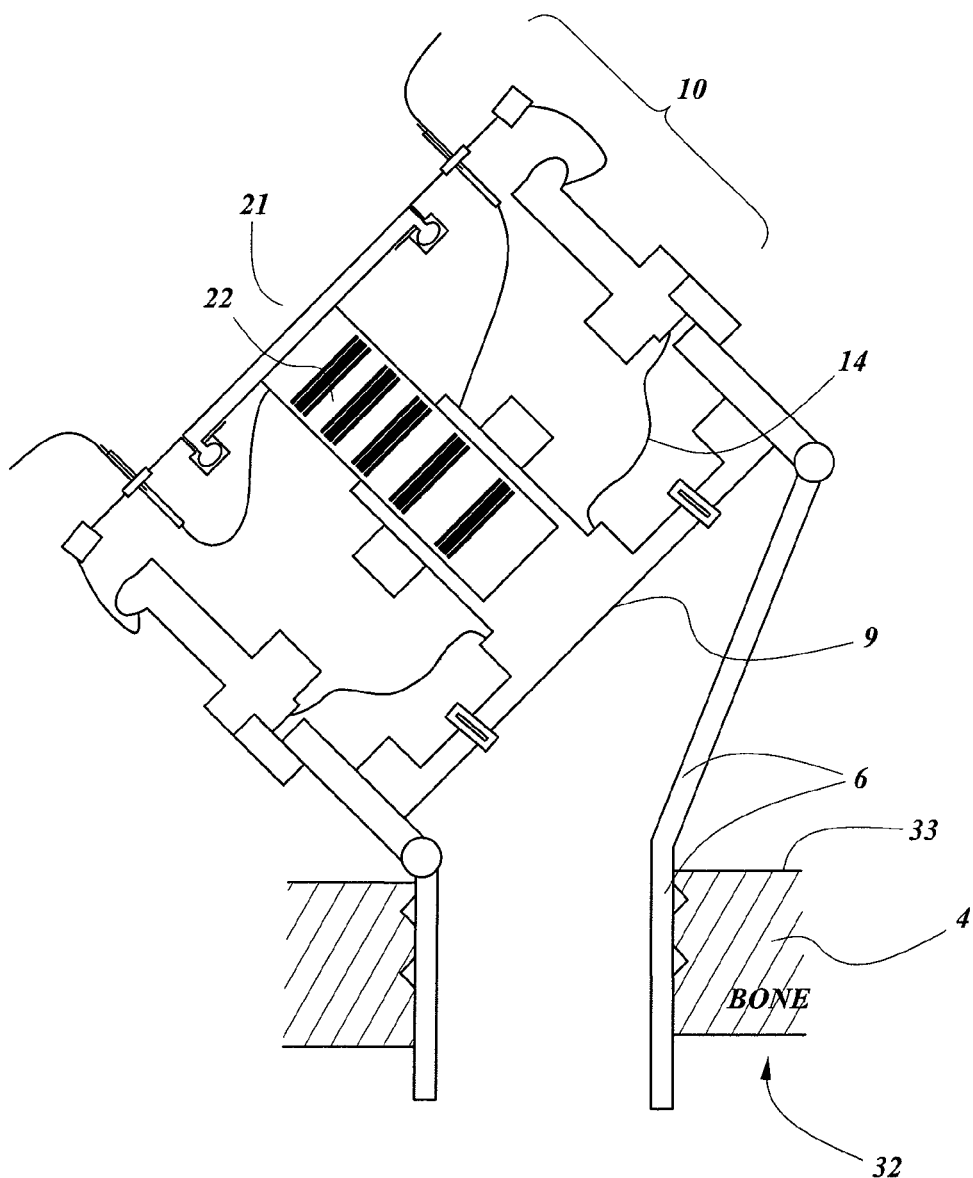
FIG. 7 illustrates in cross-section an embodiment of the combined set according to the present invention and provided with a piezo-electric sensing and/or stimulating member.

FIG. 7 is a cross-sectional drawing of another embodiment of the combined set according to the present invention and provided with a piezo-electric sensing and/or stimulating member 21. The piezo-electric transducer 22 is for example made of stress-biased lead lanthanum zirconia titanate (PLZT).

Figure 8:
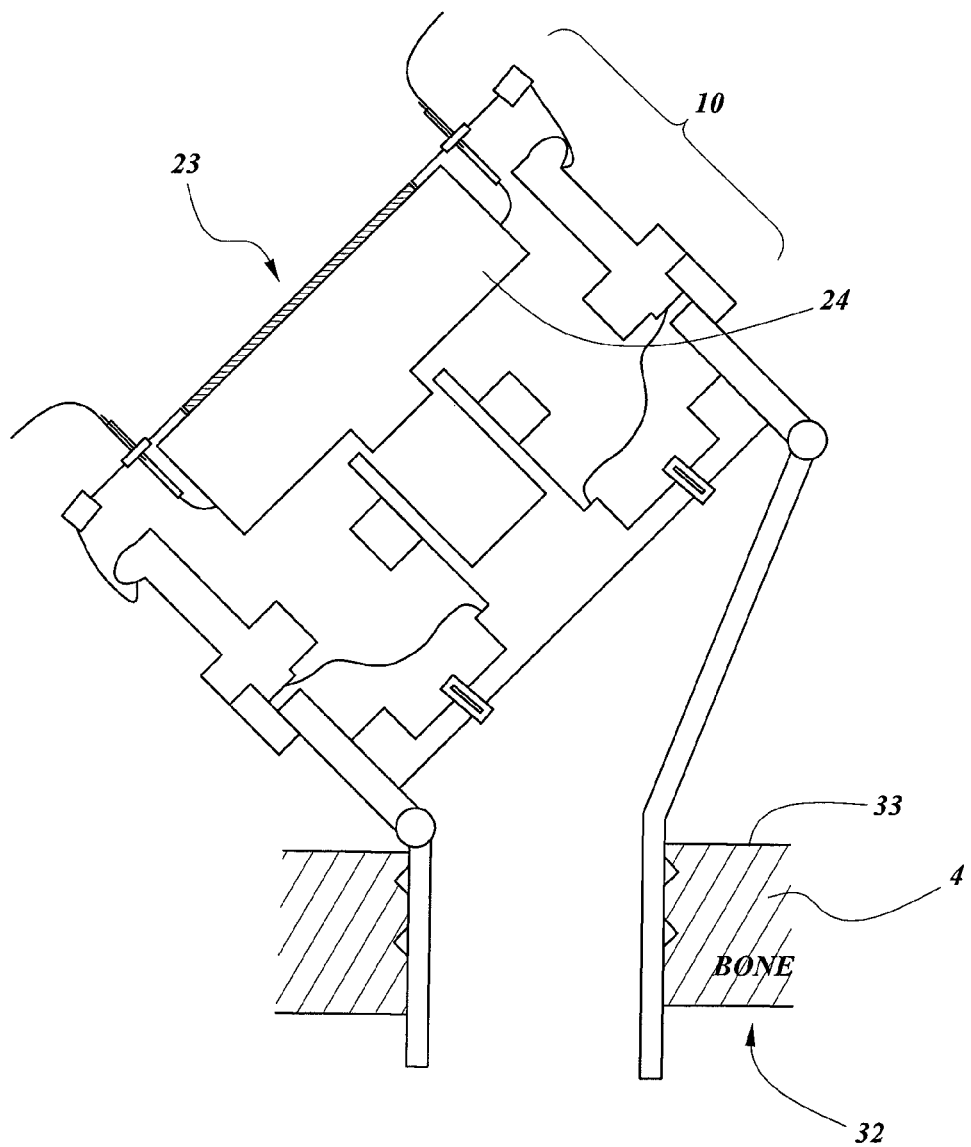
FIG. 8 shows an embodiment of the combined set according to the present invention in combination with an acoustically coupled sensing and/or stimulating element.

FIG. 8 shows another embodiment of the combined set according to the present invention and provided with an acoustically coupled sensing and/or stimulating member 23. A loudspeaker-style actuator 24 generates vibrations in the surrounding air which acoustically couple to and move the slidably movable member 9. In the reverse direction, the motions of the slidably movable member 9 may also be sensed by the actuator through acoustic coupling. The actuator 24 is, for example, a piezo-electric or electromagnetic transducer.

Figure 9:
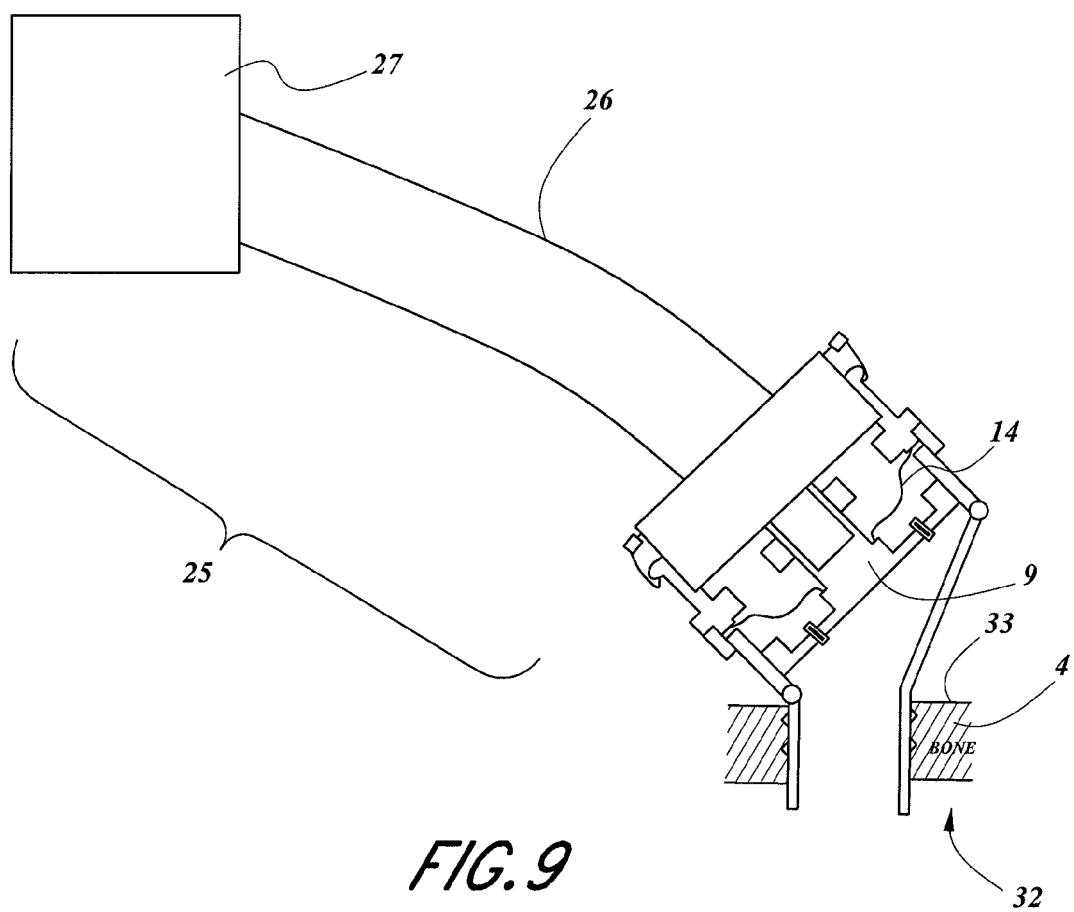
FIG. 9 shows an embodiment of the combined set according to the present invention in combination with a remote sensing and/or stimulating element.

FIG. 9 shows an embodiment of the combined set according to the present invention having a remote sensing and/or stimulating element 25. The coupling between the remote element and the slidably movable member 9 is for example realised by means of an air or liquid filled tube 26. Biocompatible liquid silicone may be used, for example, inside the tube. Tube 26 connects on one side to a remote transducer 27 and on the other side to the slidably movable member 9. The remote transducer 27 is for example a piezo-electric or electromagnetic transducer but could also be a pressure generator.

Figure 10A:
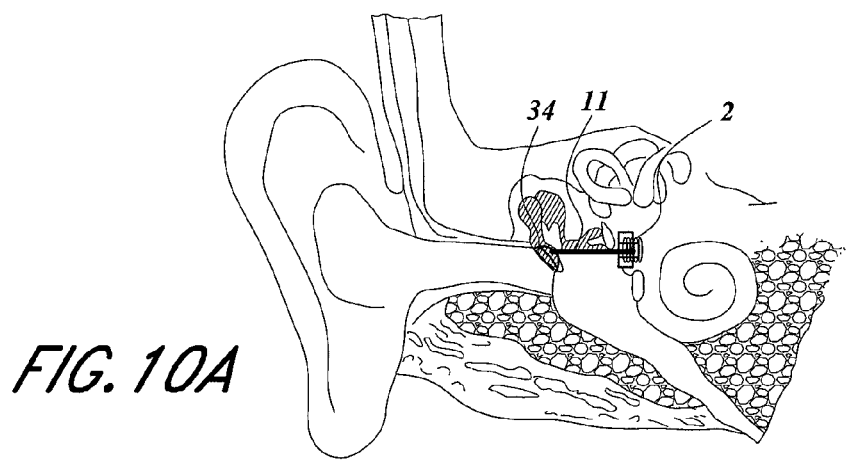
FIGS. 10A to 10C show an embodiment of the combined set with a vibration actuator comprising an interface.
Figure 10B:
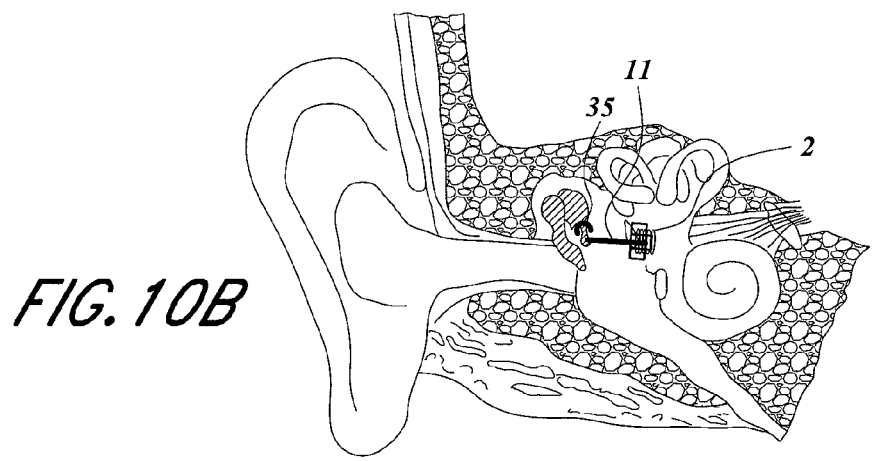

FIGS. 10A and 10B show the implantable device 2 with a vibration actuator 10 comprising an interface 11. This interface enables mechanically linking the eardrum 34 (cf. FIG. 10A) and/or any of the middle ear structures 35 (illustrated in FIG. 10B), to the slidably movable member 9. This embodiment operates in a passive mode, as there is no energy originating from an active implanted vibration source. The energy is transferred directly from either the eardrum or any of the ossicles towards the inner ear through the interface 11 and the slidably movable member 9. The total mechanical impedance of the interface and member needs to be comparable to impedance of the stapes footplate in a normal human subject, in order to transfer a comparable amount of energy under equal sound pressure levels.

Figure 10C:
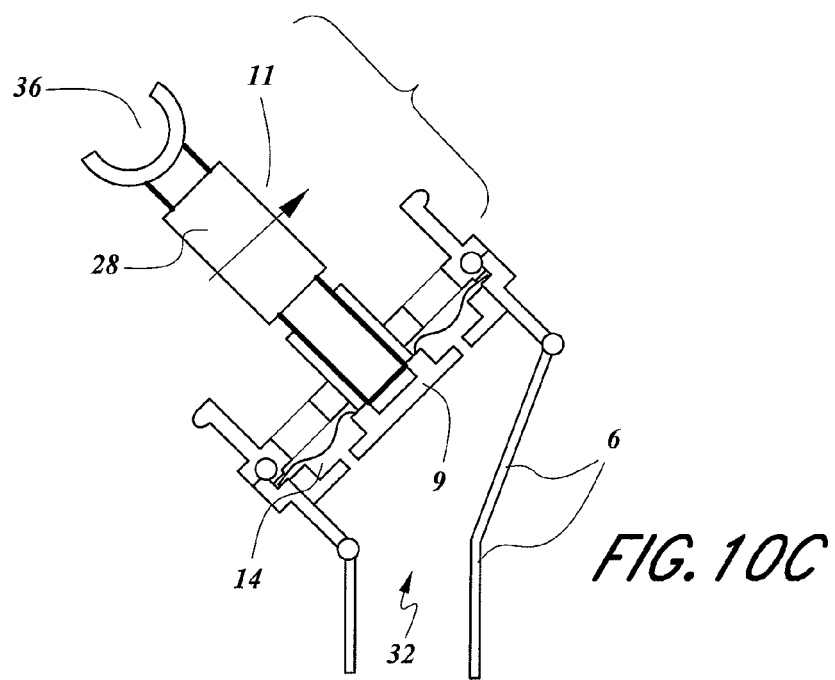

FIG. 10C shows another embodiment in which the interface 11 is adjustable in length and/or angle 28. This adjustment can be done per-operatively and allows an easier linking of the interface. The interface is provided on one side with a connective element 36 to enable the linking with for example the ear-drum and/or middle ear structures.

FIGS. 11A and 11B show a cross-section of a further embodiment of an implantable device 2 as part of a combined set according to the invention. This embodiment comprises an electrically conductive means 29 provided to apply and/or sense electric signals directly to and from the inner ear fluids.

Applying such electrical stimulation can be for instance to stimulate the inner ear neural structures. Electrical stimulation complementary to mechanical stimulation can be a significant advantage to certain oto-acoustical pathologies. In case of locally damaged inner ear structures, mechanical stimulation can be ineffective at related frequencies. For example in patients with presbyacousis where the sensory cells (hair cells) for sensing the high frequencies are damaged and no longer operate, the related neural structures are still functional and can be electrically stimulated to transfer high frequency acoustical signals.

Electrically conductive means also allows sensing various electrical potentials that are generated acoustically, electrically or by any other type of triggering signal. The sensed signals, such as the compound action potentials (CAP), cochlear microphonic (CM), etc. can be used for diagnostic purposes as well as for feed-back regulation of the sensing/stimulating implantable devices connected to the disclosed implantable device 2. In this embodiment, the member 9 is provided with an electrically conductive means 29 on its surface that faces the inner ear fluid. The electrically conductive means 29 is connected to a conductive wire 30, applied in an electrically isolated manner to the frame 6. The conductive means 29 is made, for example, of platinum or gold. Alternatively, the conductive means 29 could be obtained by direct metallization of a silicone membrane 14. The metallic frame is also conductive and forms a second electrode connected to a second conductive wire 31.

The implantable combined set can be controlled by an implantable electronic controller. This controller can, for example, be implanted in the mastoid cavity and is provided with conductive means to interface the implantable combined set.

The implantable combined set can be provided with connecting means applied to the frame 6. These connecting means being provided for connecting said vibration actuator 10 and/or a sensing member to said frame in such a manner as to enable said energy transfer. These connective means can be, for example, a click-mechanism, bayonet coupling, a screw thread or a magnetic bonding. This magnetic bonding can be realised by permanent magnets and/or electromagnets, which are coated on and/or embedded into said implantable device. The substance being for instance a Ni—Fe alloy (Permalloy) or a Nd—Fe—B alloy. This also applies to the interface 11 used in the passive mode. This set-up enables to mechanically and electrically dissociate the frame 6 from the vibration actuator 10, thus allowing connecting a large variety of actuators and/or sensing members to the implantable device. This would allow upgrading the frame, for example, at some point in the future with a newer-generation vibration actuator.

The implantable combined set can be provided with a tube element 39 allowing a transfer of substances, for example nerve-growth-factor, antibiotics or anti-inflammatory agents to and from the inner ear. A cross-section is shown in FIGS. 12A and 12B. FIG. 12A illustrates a variant of the combined set with a tube element 39 in the member 9 and FIG. 12B shows a variant with a tube element in the frame 6.

All components used in the implantable combined set and its variants can be coated with antibiotics and/or a substance promoting bone tissue growth.

The outside surface of the frame 6 of the implantable combined set and its variants can be roughened and/or provided with grooves and/or provided with a thread also to promote osseo-integration. Said surface roughness can be obtained artificially by augmenting or decreasing said surface roughness in particular with sand-blasting and/or etching and/or polishing.

The outside surface of the frame 6 of the implantable combined set and its variants can be coated with a substance provided for chemical bonding with the inner ear part and/or for mechanical anchorage in said inner ear part by expansion of said substance after insertion. This could be a ring shaped seal, for example made of silicone, which expand after insertion, for instance by absorption of inner ear fluids.

All materials used in the implantable combined set and its variants are preferably made of bio-compatible materials or can be coated with a bio-compatible substance like Titanium, Silicones, Teflon (Registered Trademark®).

What is claimed is:

1. A combined set comprising a vibration actuator and an implantable device provided to be implanted in an inner ear part formed by either a bony wall, an oval window, or a round window, said implantable device comprising:
   a surface in contact with an inner ear fluid when inserted in said inner ear part,
   a frame having an inner wall and being provided to be at least partially inserted in said inner ear part,
   a slidably movable member having an outer wall and being connected to said vibration actuator, said slidably movable member being provided for transferring energy supplied by said vibration actuator from and towards said inner ear fluid by means of a translational movement, wherein said slidably movable member is at least partially mounted inside said frame in such a manner, that a gap extending between said inner wall of said frame and said outer wall of said member is less than or equal to 0.1 mm.

2. A combined set as claimed in claim 1, wherein said implantable device comprises at least one membrane applied within said frame and extending between said inner wall and said slidably movable member.

3. A combined set as claimed in claim 2, wherein said membrane(s) and said slidably movable member are connected to each other.

4. A combined set as claimed in claim 2, characterised in wherein said membrane is corrugated and/or protuberant.

5. A combined set as claimed in claim 1, wherein said frame comprises a first segment and a second segment connected to each other.

6. A combined set as claimed in claim 5, wherein said first segment has a smaller diameter than said second segment, said first segment being provided to be implanted in an opening applied in said inner ear part.

7. A combined set as claimed in claim 5, wherein said first segment and said second segment are inclined with respect to each other.

8. A combined set as claimed in claim 5, wherein said first segment and said second segment are inclinably mounted with respect to each other.

9. A combined set as claimed in claim 5, wherein said slidably movable member is mounted inside one of said first or second segments.

10. A combined set as claimed in claim 1, wherein said slidably movable member is formed by a piston.

11. A combined set as claimed in claim 1, wherein at least a part of a surface of said member and/or of said frame are coated with a coating suitable to improve tribological and/or wear resistance properties of said implantable device.

12. A combined set as claimed in claim 1, wherein said vibration actuator comprises an interface provided for transferring vibrations generated by the middle ear structures, in particular by the eardrum.

13. A combined set as claimed in claim 1, wherein said vibration actuator is formed by an electromagnetic stimulating and/or sensing element mounted into said frame, said element comprising an electromagnetically driven actuator mechanically contacting said slidably movable member.

14. A combined set as claimed in claim 1, wherein said vibration actuator is formed by a pressure generator and/or sensing element mounted into said frame, said element being provided for driving said slidably movable member.

15. A combined set as claimed in claim 1, wherein said vibration actuator is formed by a piezoelectric stimulating and/or sensing element mounted into said frame, said element comprising a piezo-electrically driven actuator mechanically contacting said slidably movable member.

16. A combined set as claimed in claim 1, wherein said frame is dimensioned in such a manner as to insert at least partially said vibration actuator therein.

17. An implantable device as claimed in claim 1, wherein said slidably movable member and/or said frame is provided with electrically conductive means.

18. An implantable device as claimed in claim 1, wherein said slidably movable member or said frame is provided with a tube element allowing transfer of substances to and from the inner ear.

* * * * *